US007572627B2

(12) United States Patent
Rieke et al.

(10) Patent No.: US 7,572,627 B2
(45) Date of Patent: Aug. 11, 2009

(54) SYSTEM OF PROCESSING MIXED-PHASE STREAMS

(75) Inventors: James F. Rieke, Naperville, IL (US); Timothy J. Rittof, West Chicago, IL (US)

(73) Assignee: United States Filter Corporation, Palm Desert, CA (US)

( * ) Notice: Subject to any disclaimer, the term of this patent is extended or adjusted under 35 U.S.C. 154(b) by 894 days.

(21) Appl. No.: 10/619,280

(22) Filed: Jul. 14, 2003

(65) Prior Publication Data

US 2004/0037933 A1 Feb. 26, 2004

Related U.S. Application Data

(60) Provisional application No. 60/396,421, filed on Jul. 16, 2002.

(51) Int. Cl.
*C12M 1/02* (2006.01)

(52) U.S. Cl. ........................ 435/293.2; 165/58; 165/64; 165/120; 165/125; 165/184

(58) Field of Classification Search .............. 435/293.2; 165/58, 64, 120, 125, 184
See application file for complete search history.

(56) References Cited

U.S. PATENT DOCUMENTS 3,898,745 A 8/1975 Carlsson
4,182,400 A 1/1980 de Nevers
4,756,361 A 7/1988 Lesage
4,814,189 A * 3/1989 Laude-Bousquet ........... 426/15
5,043,284 A * 8/1991 Welledits et al. .............. 426/16
5,242,016 A 9/1993 Voss et al.
5,284,203 A 2/1994 Dauvargne
5,299,635 A 4/1994 Abraham
5,307,867 A 5/1994 Yasuda et al.
5,318,111 A 6/1994 Young et al.
5,323,849 A 6/1994 Korczynski, Jr. et al.
5,323,850 A 6/1994 Roberts
5,323,851 A 6/1994 Abraham
5,329,995 A 7/1994 Dey et al.
5,341,872 A 8/1994 Mercurio
5,348,083 A 9/1994 Hosoya et al.

FOREIGN PATENT DOCUMENTS

DE 4121873 A1 1/1993
DE 43 00 011 A1 7/1994
FR 2295394 7/1976
FR 2439552 * 5/1980

(Continued)

OTHER PUBLICATIONS

Arthur E. Bergles, "Augmentation of Heat Transfer," 2.5 Single-Phase Convective Heat Transfer, 2.5.11-1-2.5.11-12, 1983 Hemisphere Publishing Corporation.

(Continued)

*Primary Examiner*—Anthony Weier
(74) *Attorney, Agent, or Firm*—Coats & Bennett, P.L.L.C.

(57) ABSTRACT

Heat transfer in non-turbulent highly viscous mixed-phase flowing streams can be improved by altering flow characteristics using spiral-shaped elements to eliminate boundary phenomena. The spiral-shaped element promotes helical or spiral flow paths to reduce or eliminate temperature gradients associated with laminar flow characteristics.

15 Claims, 5 Drawing Sheets

FOREIGN PATENT DOCUMENTS

| | | | |
|---|---|---|---|
| FR | 2608380 | | 6/1988 |
| GB | 424236 | A | 2/1935 |
| GB | 1076587 | | 7/1967 |
| GB | 1146564 | | 3/1969 |
| JP | 11-90401 | * | 4/1999 |
| WO | WO 98/04879 | A1 | 2/1998 |

OTHER PUBLICATIONS

Arthur E. Bergles, "Augmentation of Condensation," 2.6 Condensation, 2.6.6-1-2.7.9-5, 1983 Hemisphere Publishing Corporation.

W.J. Marner et al., "Augmentation of Highly Viscous Laminar Heat Transfer Inside Tubes with Constant Wall Temperature," *Experimental Thermal and Fluid Science* 1989; 2:252-267; 1989 by Elsevier Science Publishing Co., Inc., New York, NY.

R.S. Van Rooyan et al., "Laminar Flow Heat Transfer in Internally Finned Tubes With Twisted-Tape Inserts," p. 577-581, University of Stellenbosch, Stellenbosch, South Africa, 1978.

D.R. Oliver et al., "Heat Transfer Enhancement in Round Tubes Using Wire Matrix Turbulators: Newtonian and Non-Newtonian Liquids," *Chem. Eng. Res. Des.*, vol. 66, Nov. 1988, pp. 555-565.

"Fine-Fin" Product Literature, publication date unknown.

"Heat Exchanger Tubes with Increased Heat Transfer," VDM Tube Division 1978.

P.J. Marto et al., "An Experimental Comparison of Enhanced Heat Transfer Condenser Tubing," pp. 1-9, Department of Mechanical Engineering, Naval Postgraduate School, Monterey, California, publication date unknown.

M.H. Mehta et al., "Heat Transfer and Frictional Characteristics of Spirally Enhanced Tubes for Horizontal Condensers," pp. 11-21, Gujarat State Fertilizers Co. Ltd. Baroda, India; Department of Chemical Engineering, Indian Institute of Technology, Powai, Bombay, India, publication date unknown.

T.C. Carnavos, "Heat Transfer Performance of Internally Finned Tubes in Turbulent Flow," pp. 61-67, Noranda Metal Industries, Inc., Forge-Fin Division, Newtown, Connecticut, publication date unknown.

R.L. Webb et al., "A Parametric Analysis of the Performance of Internally Finned Tubes for Heat Exchanger Application," Department of Mechanical Engineering, The Pennsylvania State University, University Park, Pennsylvania, pp. 69-77, publication date unknown.

T.C. Scott et al., "Accurate, Simple Expressions for the Efficiency of Single and Composite Extended Surfaces," Mechanical and Aerospace Engineering, University of Virginia, Charlottesville, Virginia, pp. 79-85, publication date unknown.

H.M. Soliman, "The Effect of Fin Material on Laminar Heat Transfer Characteristics of Internally Finned Tubes," Department of Mechanical Engineering, University of Manitoba, Winnipeg, Manitoba, Canada, pp. 95-102, publication date unknown.

R.K. Gupta et al., "Heat Transfer and Friction Characteristics of Newtonian and Power-Law Type of Non-Newtonian Fluids in Smooth and Spirally Corrugated Tubes," Solar Energy Division, Jyoti Ltd., Baroda, India; Department of Chemical Engineering, Indian Institute of Technology, Bombay, India, pp. 103-113.

A.E. Bergles, "Chapter 3—Techniques to Augment Heat Transfer," pp. 3-1-3-80, *Handbook of Heat Transfer Applications*, Second Edition, McGraw-Hill Book Company 1985.

T.J. Rabas, "Selection of the Energy-Efficient Enhancement Geometry for Single-Phase Turbulent Flow Inside Tubes," 1989 National Heat Transfer Conference, HTD-vol. 108, Heat Transfer Equipment Fundamentals, Design, Applications and Operating Problems, 1989, pp. 193-204.

R. Antonelli et al., "Design and Application Considerations for Heat Exchangers with Enhanced Boiling Surfaces," *Evaporation and Condensation*, 1983, pp. 175-191.

V.H. Morcos, "Performance of Shell-And-Dimpled-Tube Heat Exchangers for Waste Heat Recovery," *Heat Recovery Systems & CHP*, vol. 8, No. 4, pp. 299-308, 1988, Pergamon Press plc, Great Britain.

R. Wiltz, "Engineered Products and Good Design Combine to Improve HX Performance," reprinted from *Chemical Processing* Sep. 1992.

S. Yilmaz et al., "Performance of Finned Tube Reboilers in Hydrocarbon Service," The American Society of Mechanical Engineers, New York, NY, publication date unknown.

J.A. Moore, "Fintubes Foil Fouling for Scaling Services," pp. 8-10, *Chemical Processing* Aug. 1974.

* cited by examiner

SYSTEM OF PROCESSING MIXED-PHASE STREAMS

CROSS-REFERENCE TO RELATED APPLICATION

This application claims the benefit under 35 U.S.C. § 119 (e) of U.S. Provisional Patent Application Ser. No. 60/396,421 filed on Jul. 16, 2002, which is incorporated herein by reference in its entirety.

BACKGROUND OF THE INVENTION

1. Field of the Invention

The present invention is directed to operations involving mixed-phase streams and, more particularly, to the processing of mixed-phase streams comprising biomaterial and the concentration of biomaterial streams and other fermentation waste by enhancing heat transfer unit operations.

2. Description of Related Art

Turbulent flow during heat transfer in heating unit operations in the petroleum, chemical, food and other related industries can improve heat transfer. Laminar flow, in contrast, can have less or reduced heat transfer rates. Thus, techniques have been used to improve heat transfer by increasing the effective heat transfer area and/or by promoting turbulent flow.

Other techniques attempt to disrupt laminar flow characteristics. For example, Oliver et al., in "Heat Transfer Enhancement in Round Tubes Using Wire Matrix Turbulators: Newtonian and Non-Newtonian Liquids," Chem. Eng. Res. Des., v. 66, p. 553-565, November 1988, describe using a central wire core onto which a series of wire loops are wound such that each loop is inclined at an angle to the core. It is inserted into a tube such that the loops come into close contact with the tube wall. The loops appear to disturb fluid flow near the tube wall and promote radial mixing as the fluid flows through the mesh of loops.

Also, Marner et al., in "Augmentation of Highly Viscous Laminar Heat Transfer Inside Tubes with Constant Wall Temperature," Experimental Thermal and Fluid Science, 2:252-267 1989, report of tube flow and heat transfer under laminar flow conditions in a plain tube, an internally finned tube, and a tube with a twisted-tape insert van Rooyen et al., in "Laminar Flow Heat Transfer in Internally Finned Tubes with Twisted-Tape Inserts," p. 577-581, University of Stellenbosch, Stellenbosch, South Africa 1978, studied heat transfer and pressure drop for laminar flowing oil in smooth and internally finned tubes with twisted-tape inserts.

BRIEF SUMMARY OF THE INVENTION

The present invention, in one or more embodiments, can provide improvements in mixed-phase stream unit operations resulting in, inter alia, enhanced heat transfer, reduced power requirement, as well as reduced overall utility loading and, hence, environmental liability while potentially increasing processing capacity.

The invention can promote concentration of a viscous mixed-phase stream or fluid. Viscosity is a function of composition, temperature, and total solids. The present invention provides relative processing improvements for facilities. For example, at one facility, the present invention may allow concentration to as much as about 40% total solids (TS) whereas conventional, unmodified operations may allow only up to as much as 25% TS; and in another facility, the present invention may allow as much as 70% TS whereas in the unmodified facility only up to 50% TS may be possible.

Thus, in accordance with one or more embodiments, the present invention provides a method of processing a mixed-phase stream. The method comprises steps of introducing the mixed-phase stream into a heat exchanger and inducing the mixed-phase stream into a spiral flow path.

In accordance with one or more embodiments, the present invention provides a method of increasing solids concentration in a biomaterial stream having solid and liquid fractions. The method comprises steps of inducing non-turbulent spiral flow within a heat exchanger tube, heating the biomaterial stream, and vaporizing at least a portion of the liquid fraction from the biomaterial stream.

In accordance with one or more embodiments, the present invention provides a system for processing a biomaterial stream. The system comprises a biomaterial source in communication with a heater comprising a spiral-shaped element disposed in at least one heater tube.

In accordance with one or more embodiments, the present invention provides a system for processing biomaterial. The system comprises a grain handling unit operation, a grain fermentation unit operation in communication with the grain handling unit operation, a distillation unit operation in communication with the fermentation unit operation, an evaporation unit operation in communication with the distillation unit operation, and a concentrator in communication with the evaporation unit operation, the concentrator comprising a heat exchanger comprising a spiral-shaped element disposed within a tube of the heat exchanger.

In accordance with one or more embodiments, the present invention provides a system for processing grain. The system comprises a grain steeping unit operation, a grinding unit operation downstream of the grain steeping unit operation, a germ separation unit operation downstream of the grinding unit operation, filtration and washing unit operations receiving material from the germ separation unit operation, and a concentrator receiving heavy steep stream from the grain steeping unit operation, the concentrator comprising a heat exchanger comprising a spiral-shaped element disposed within a tube of the heat exchanger.

In accordance with one or more embodiments, the present invention provides a method of improving the heat transfer properties of a heat exchanger comprising installing an element into at least one tube of the heat exchanger that can induce a mixed-phase stream flowing therein into a spiral flow path.

Other advantages and features of the invention will be apparent from the detailed description of the invention when considered with the accompanying drawings, which are schematic and not drawn to scale. In the figures, each identical or substantially similar component is referenced or labeled by a numeral or notation. For clarity, not every component is labeled in every figure nor is every component of each embodiment of the invention shown where illustration is not necessary to allow those of ordinary skill in the art to understand the invention.

BRIEF DESCRIPTION OF THE DRAWINGS

Non-limiting embodiments of the invention will be described by way of example with reference to at least some of the accompanying drawings, in which:

FIG. 5A is a view at section 5*a*-5*a* of FIG. 4, FIG. 5B is a view at section 5*b*-5*b* of FIG. 4, FIG. 5C is a view at section 5*c*-5*c* of FIG. 4, and FIG. 5D is a view at Section 5*d*-5*d* of FIG. 4.

DETAILED DESCRIPTION OF THE INVENTION

Figure 1:
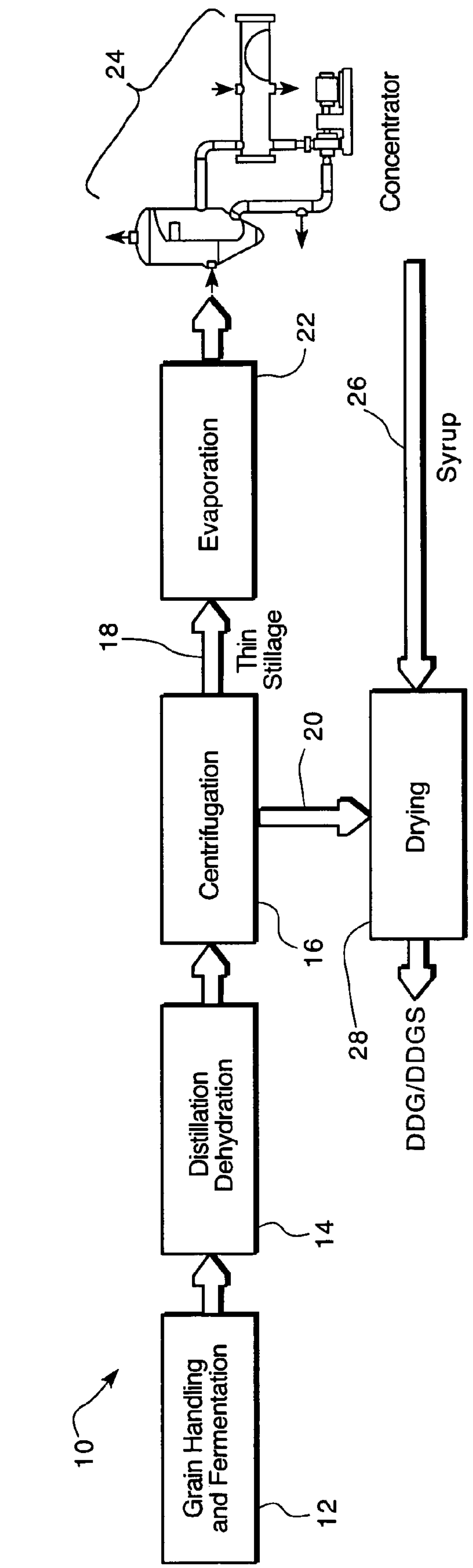
FIG. 1 is a flow diagram showing a dry milling process in a grain ethanol processing system in accordance with one or more embodiments of the invention.

U.S. Provisional Patent Application Ser. No. 60/396,421 filed on Jul. 16, 2002 is incorporated herein by reference in its entirety.

The present invention is directed to processes involving energy transfer of laminar-flowing streams. In one or more aspects, the present invention involves improving heat transfer characteristics of a stream in a heating unit operation. In one or more aspects, the present invention provides improved unit operations during the concentration of mixed-phase streams, including, but not limited to, the heating of biomaterial streams. In one or more aspects, the present invention involves heat exchange unit operations having one or more spiral-shaped elements that promote non-turbulent flow. In one or more aspects, the present invention provides an increase of the concentration of mixed-phase streams, such as but not limited to biomaterial streams, by at least about 50% total solid or even as much as 80% total solids as well as improved heat transfer, reduced horsepower requirements and increased effective processing capacity.

The present invention can provide a system and a method of increasing the concentration of solid materials in processing of a mixed-phase stream such as, but not limited to a stream comprising biomaterial. Thus, in accordance with one or more embodiments, the present invention provides methods of increasing solids concentration in a mixed-phase stream. The methods can comprise steps of introducing the stream into a heat exchanger and inducing the stream into a spiral flow path. The method can further comprises a step of heating at least a portion of the mixed-phase stream. The method can further comprise a step of vaporizing any volatile component from mixed-phase stream to produce a substantially dry solid product. The substantially dry solid product may be suitable for animal feed. For example, the biomaterial can comprise stillage such as from a grain, e.g. corn, processing facility. The step of inducing spiral flow can comprise allowing the stream to flow by a spiral-shaped element. For example, the stream can be induced into a spiral flow path by introducing it into a tube of a heater having disposed therein a unitary spiral-shaped element.

In accordance with one or more embodiments, the methods of the present invention can comprise steps of inducing non-turbulent spiral flow within a heat exchanger tube, heating the biomaterial stream having liquid and solid fractions, and vaporizing at least a portion of the liquid fraction from the biomaterial stream. The methods can further comprise a step of drying the biomaterial stream to produce substantially dry solid product.

In accordance with one or more embodiments, the present invention provides a system for processing a biomaterial stream. The system can comprise a biomaterial source in communication with a heater comprising a spiral-shaped element disposed in at least one heater tube. The spiral-shaped element can have a width spanning less than an inside diameter of the heater tube. For example, the width can span less than about 50% of the inside diameter. The system can be utilized to process biomaterial from a grain processing facility, which can have one or more grain handling, fermentation, distillation, and dehydration operations.

In accordance with one or more embodiments, the present invention provides a system for processing biomaterial. The system comprises a grain handling unit operation, a grain fermentation unit operation in communication with the grain handling unit operation, a distillation unit operation in communication with the fermentation unit operation, an evaporation unit operation in communication with the distillation unit operation, and a concentrator in communication with the evaporation unit operation, the concentrator comprising a heat exchanger comprising a spiral-shaped element disposed within a tube of the heat exchanger.

In accordance with one or more embodiments, the present invention provides a system for processing grain. The system comprises a grain steeping unit operation, a grinding unit operation downstream of the grain steeping unit operation, a germ separation unit operation downstream of the grinding unit operation, filtration and washing unit operations receiving material from the germ separation unit operation, and a concentrator receiving heavy steep stream from the grain steeping unit operation, the concentrator comprising a heat exchanger comprising a spiral-shaped element disposed within a tube of the heat exchanger.

In accordance with one or more embodiments, the present invention provides a method of improving the heat transfer properties of a heat exchanger comprising installing an element into at least one tube of the heat exchanger that can induce a mixed-phase stream flowing therein into a spiral flow path. The element can comprise a spiral-shaped element spanning at least a portion of the tube. The element can have an aspect ratio that is about 5. Installing the element can comprise inserting a ribbon into the heat exchanger tube and winding the ribbon to twist the ribbon by at least one rotation.

In accordance still other embodiments, the present invention provides a system for processing a biomaterial stream comprising a stillage material source in communication with a heater comprising a spiral-shaped element in at least one heater tube. The spiral-shaped element typically has a width spanning less than about 50% of inside diameter of the heater tube. In accordance with further embodiments, the present invention provides a system for processing stillage material. The system can comprise a stillage material source, an evaporator in communication with the stillage material source, a concentrator in communication with the evaporator, the evaporator comprising a heat exchanger comprising a spiral-shaped element disposed within a tube of the heat exchanger, and a dryer in communication with the concentrator. The internal element can be sized to permit internal cleaning by, for example, the use of a hydroblasting lance.

Furthermore, the present invention can provide for an increase of concentration of total solids in a mixed-phase stream as the viscosity of such streams increase. For example, the present invention can be directed at processing operations of mixed-phase streams, such as increasing the solids concentration of biomaterial streams, which typically have viscosities greater than about 50 cP, to at least about 50% and, in some cases, at least about 60% or even at least about 70% or as much as at least about 80%, increasing viscosities of at least about 100 cP, at least about 200 cP, at least about 400 cP, at least about 500 cP, or even at least about 600 cP. It is to be understood that the solids concentrations and associated viscosities of the mixed phase streams can vary according to several factors including, but not limited to the temperature, flow rates and composition of the various streams in the system.

Figure 2:
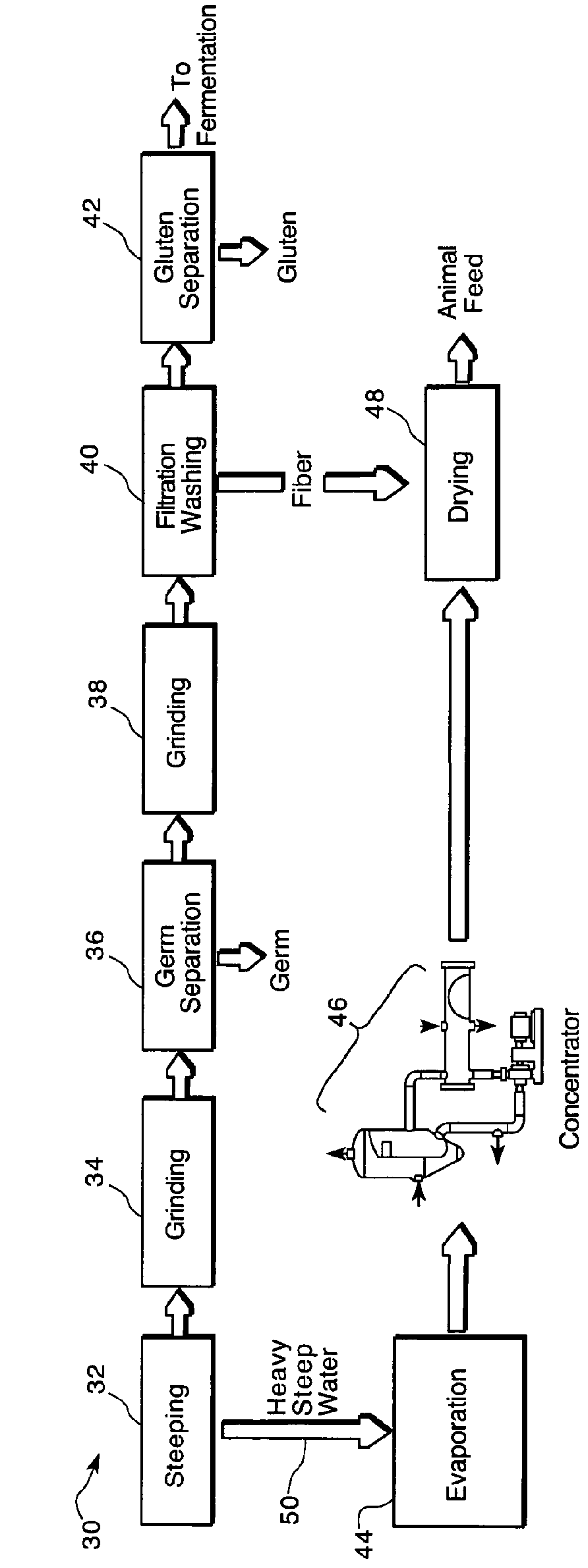
FIG. 2 is a flow diagram showing a wet milling process in a grain ethanol processing system in accordance with one or more embodiments of the invention.

FIGS. 1 and 2 are relevant to one or more embodiments of the present invention. FIG. 1 shows a process flow diagram of a dry-milling grain ethanol processing system relevant to one or more embodiments of the present invention. The dry-milling system 10 can comprise one or more grain handling and fermentation unit operations 12, distillation and/or dehydration unit operations 14, centrifugation unit operations 16 typically producing a thin stillage stream 18 and other waste streams such as solids stream 20. Thin stillage stream 18 is typically processed in an evaporation unit operation 22 and/or a stillage concentrator unit operation 24 to produce a syrup stream 26 that typically has greater solids concentration relative to thin stillage stream 18. Further processing operations can include a drying unit operation 28 that can ultimately dry any solids products.

FIG. 2 shows a process flow diagram of a wet-milling grain ethanol processing system relevant to one or more embodiments of the present invention. The wet-milling system 30 can comprise one or more steeping unit operations 32, grinding unit operations 34, germ separation unit operations 36, additional grinding unit operations 38, filtration and/or washing unit operations 40, and gluten separation unit operations 42. Wet-milling system 30 can comprise one or more evaporation unit operations 44 as well as stillage concentrator unit operations 46 and drying unit operations 48.

In the dry-milling process, for example, waste biomaterial from the distillation/dehydration unit operations 14 can be further separated to produce thin stillage stream 18 as well as solids-rich stream 20. Thin stillage stream 18 typically comprising biomaterial can be further processed to increase solids concentration by further processing in evaporation and stillage concentrator unit operations 22 and 24, respectively. The relatively higher solids concentrations biomaterial-containing, syrup stream 26 can be still further processed to produce dry solids in one or more drying unit operations 28. Such solids can be disposed or utilized as animal feed. Likewise, mixed-phase biomaterial-containing stream 50 from one or more steeping unit operations 32 of the wet-milling system 30 can be further processed to increase its solid concentration before drying. As shown in FIG. 2 and in similar to the process shown in FIG. 1, the biomaterial-containing stream 50 can be processed in one or more evaporation and stillage concentrator unit operations 44 and 46, respectively. It should be noted that for illustrative purposes, the reference to as biomaterial-containing streams is for illustrative purposes only and as such are representative of mixed-phase streams that typically comprise one or more solid components and one or more miscible or immiscible liquid components.

Figure 3:
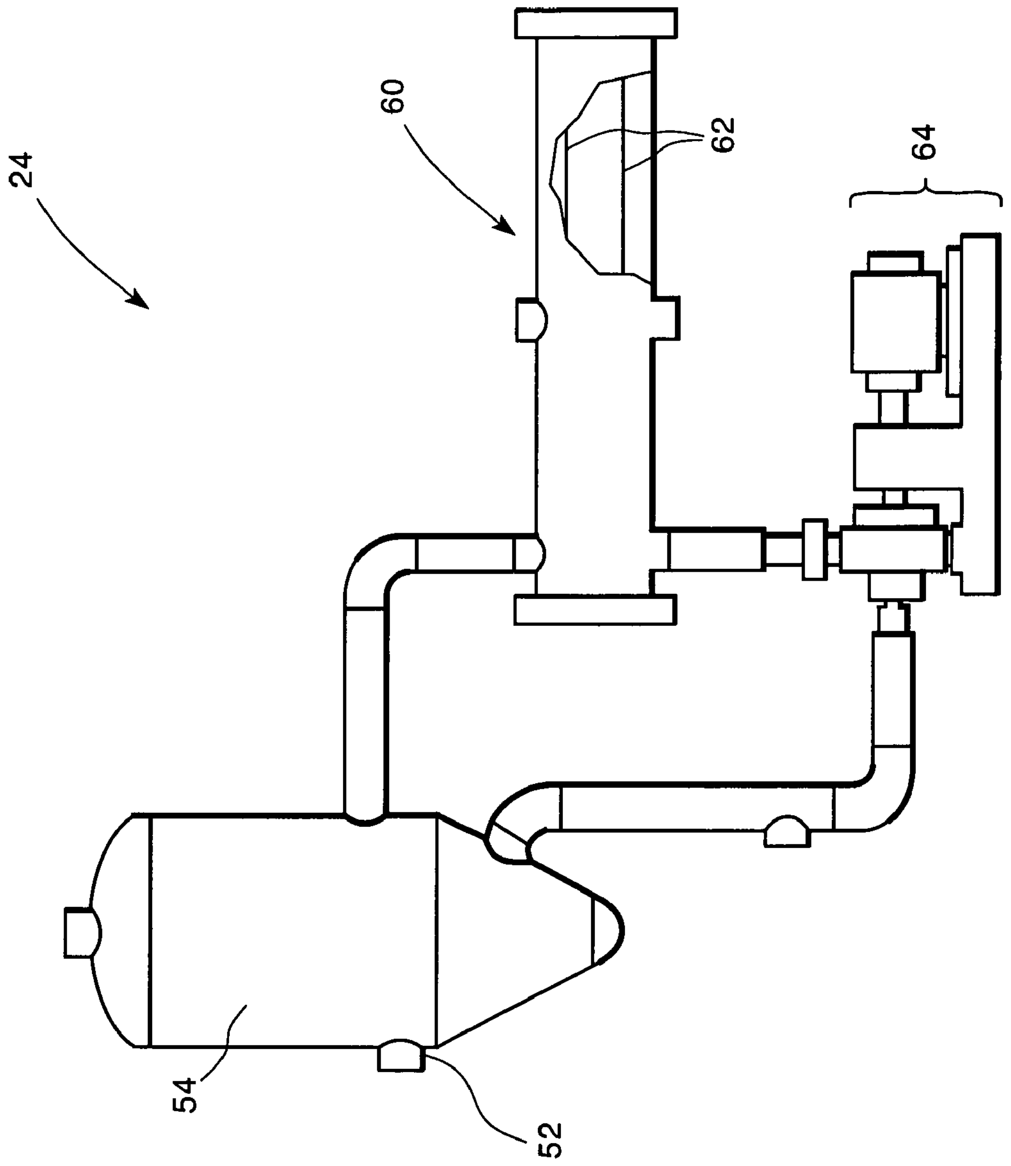
FIG. 3 is a schematic diagram showing a concentrator in accordance with one or more embodiments of the invention.

In accordance with one or more embodiments of the present invention, stillage concentrator unit operations 24 and 46, shown schematically in FIG. 3, typically comprise fluid connections 52 from the evaporators to one or more flash vessels 54. Stillage unit operations 24 and 46, can further include one or more heating unit operations 60 typically having one or more heating elements 62, such as heating tubes through which the biomaterial stream typically flows through. Stillage operations 24 and 46 typically include one or more transfer units 64, such as pumps capable of promoting circulation of the biomaterial stream between vessel 54 and heater 60 or to drying unit operation 28. Heater 60 can be any process equipment or system capable of effecting heat transfer to and/or from any stream including, but not limited to, the biomaterial-containing stream. For example and in accordance with one or more embodiments, heater 60 comprises one or more shell-and-tube heat exchangers. In such an arrangement, the biomaterial stream typically runs through the tube-side and a heating medium, such as steam, or other process stream, typically runs through the shell-side. Another example of a process equipment or system suitable as heater 60 includes gas or oil-fired heaters. As with shell-and-tube heat exchangers, the biomaterial stream typically runs through the tubes of such fired heaters.

Heat transfer to the biomaterial stream can be influenced by several factors such as, but not limited to, the temperature difference between the heating medium and the heated stream, the effective heat transfer area as well as the effective heat transfer coefficient. Streams having laminar flow characteristics can have lower heating rates than streams having turbulent flow characteristics because, it is believed, of the temperature gradient associated with such laminar flow. In one or more embodiments, the present invention can be relevant to improving heat transfer in streams having laminar flow characteristics. Thus, in one or more embodiments, the present invention provides an insert that can be installed in one or more heat exchange tubes to eliminate or at least reduce the influence of laminar flow influence.

In accordance with one or more embodiments, the present invention provides an insert, preferably a spiral-shaped element, in a heat exchanger tube that can induce a spiral flow path within the tube. For example and as shown in the embodiment depicted in FIG. 4, a spiral-shaped element 66 can be disposed in a heating element 62 to direct or at least promote the fluid or stream 68 typically flowing in heating element 62 into a spirally-shaped flow path, designated by reference 70. In accordance with one or more embodiments of the present invention, spiral-shaped element 66 can promote increased heat transfer rate in non-turbulent, laminar flowing streams by, for example, eliminating or at least reducing any laminar flow boundary velocity profiles. In some embodiments, spiral-shaped element 66 reduces or eliminates such laminar velocity profiles without creating any obstruction to flow that would promote turbulent flow characteristics. Thus, in accordance with one or more embodiments, spiral-shaped insert 66 can reduce or eliminate any radial temperature gradients in the heated fluid without any pressure drop typically associated with obstructive features that promote turbulent flow characteristics. It should be noted however, that the features and advantages of the present invention are not limited to streams having laminar flow characteristics and can be suitable for streams having turbulent flow characteristics.

Spiral-shaped element 66 can be defined by, among other characteristics, width, pitch and gauge. For example, the width of element 66 can span across the inside dimension, such as the inside diameter, of heating element 62 but can span less than about 75% of the inside dimension of heating element 62. In some cases, the width can span less than about 50% of the inside dimension of heating element 62 but other cases, the width can span less than about 25%. The thickness or gauge of element 66 can vary depending on several factors such as, but not limited to, the physical considerations associated with installation and service. Likewise, the pitch of the helix defined by the spiral-shaped element can depend on several factors including, but not limited to, the physical properties of the mixed-phase stream to the extent necessary to induce a spiral flow path with or without promoting turbulent flow characteristics or introducing additional pressure inefficiencies as well as in the effectiveness relative to eliminating or reducing any boundary layer effects.

The width can depend on several design factors including, but not limited to mechanical strength considerations during installation as well as service, the necessity to perform routine cleaning operations and, thus, the size of cleaning apparatus that would be introduced into heating element 62, and the size characteristics of any solid components that could be present if mixed-phase streams are introduced into heating element 62. For example, element 66 can have a spiral shape, helically-winding along at least a portion of the length of heating element 62 with a width that would provide an unobstructed pathway having dimension d that would allow insertion of a cleaning apparatus, such as a hydroblasting lance (not shown) through heating element 62. Element 66 can have a particular height ratio or flight to diameter ratio that would be dependent on particular operating conditions including, but not limited to, the composition, viscosity, density, surface tension, heat capacity or other physical property of the heated stream. Other factors that may be relevant to the configuration of element 66 include, but are not limited to, the size, shape and geometrical aspects of any solid components in the mixed-phase stream. As used herein, pitch refers to the number of spirals or turns of element 66 and pitch density refers to the number of spirals or turns per unit length of element 66.

The width can vary, randomly or regularly, along the length of element 62 to provide an unobstructed pathway having a varying dimension. Varying the width can be advantageous in varying the pitch along the length of element 62 installed or as it is installed in place. For example, the regions element 62 can have a relatively higher pitch corresponding to regions having less width because, it is believed, such regions may resist twisting. It is noted, however, that the resistance to twisting can be affected by other factors, including but not limited to, the thickness of element 62. The thickness can thus be varied along with at least any one of the pitch and width of element 62. As with the width, the thickness can be varied randomly or regularly, depending on the design considerations associated with particular installation facilities. Thus, in accordance with one or more embodiments, the thickness can be varied in regions having greater relative widths to control the pitch around such regions. As used herein, the term pitch refers to the number of spirals or twists and the pitch density refers to the number or spirals or twists per unit length.

Figure 4:
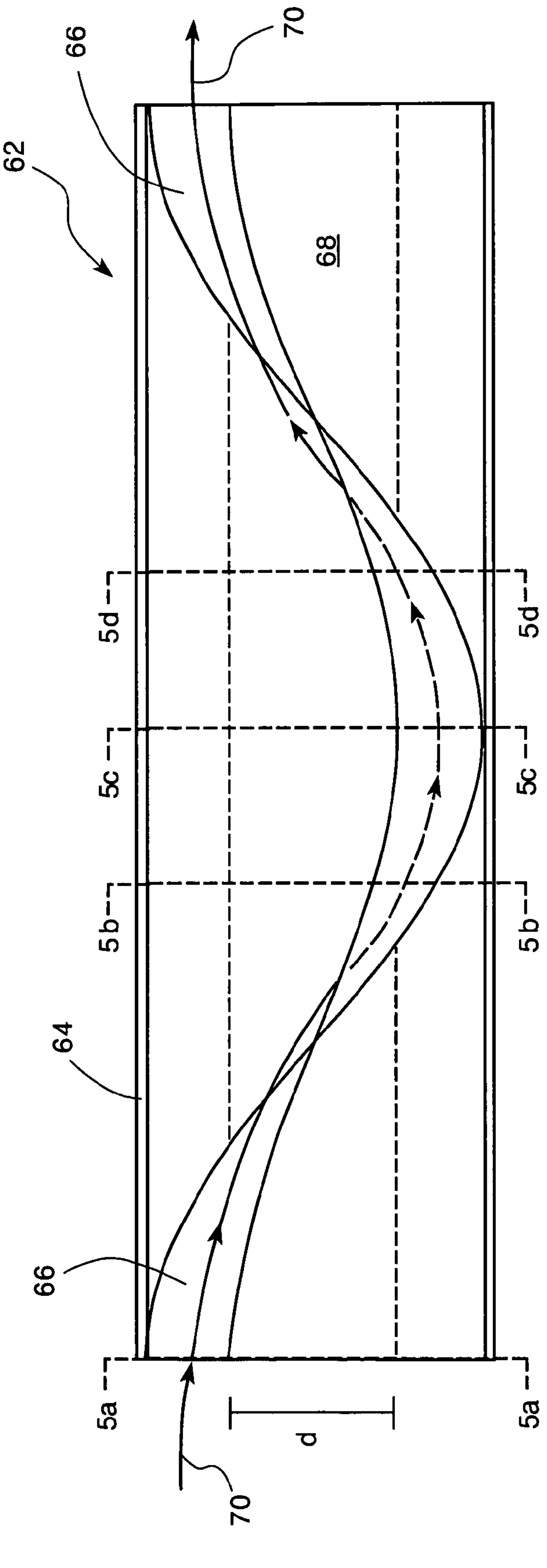
FIG. 4 is a sectional view of a portion of a tube showing an element in accordance with one or more embodiments of the invention.

As shown in FIG. 4, the element 66 can have a tendency to unwind and may do so outside the confines defined by heating element 62. Installation of element 66 can be effected by elongating/stretching element 66 to reduce the effective outer dimension of element 66 and permit unobstructed insertion within heating element 62. When element 66 has been positioned as desired, the applied force effecting elongation can be release to allow retraction of element 66 and confinement within the bounds of heating element 62. Thus, element 66 can be secured by compression fit within heating element 62.

In accordance with one or more embodiments, the element 66 can comprise a ribbon installed within at least one tube of a heat exchanger. Installation of the ribbon can comprise inserting it into, at least partially, a heat exchanger tube and imparting a twist, typically along the lengthwise axis or direction, by at least one rotation. The ends of the twisted ribbon may be secured to maintain the spiral orientation thus imparted by utilizing techniques known in the art such as, but not limited to, welding or by using adhesive compounds.

Figure 5D:
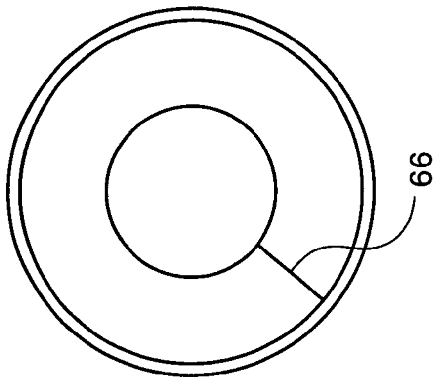
FIGS. 5A-5D are illustrations at various positions along the length of the sectional view of FIG. 4 where
Figure 5C:
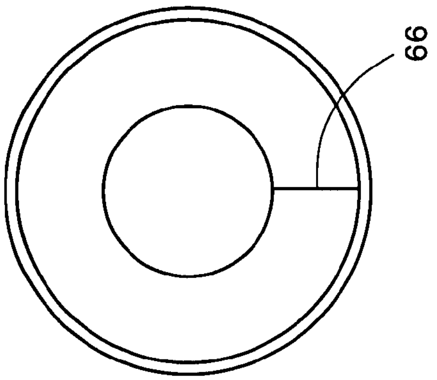
Figure 5B:
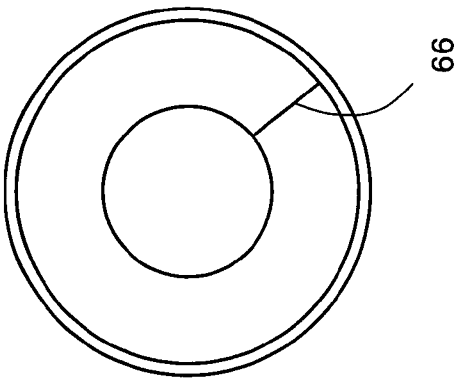
Figure 5A:
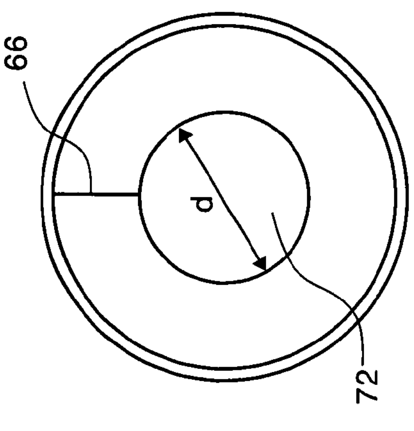

FIGS. 5A-5D show various end-views along the length of element 62 with element installed therein and as indicated in FIG. 4. FIG. 5A is an end-view of FIG. 4 at section 5a-5a; FIG. 5B is an end-view of FIG. 4 at section 5b-5b; FIG. 5C is an end-view of FIG. 4 at section 5c-5c; and FIG. 5D is an end-view of FIG. 4 at section 5d-5d. FIGS. 5A-5D show element 66 as it twists or spirals along the length of element 62. FIGS. 5A-5D show element 66 defining a region along the inside of element 62 as well as a free, unoccupied region 72, shown as having a diameter d. Typically, the degree of curvature of element 66 permits a gradual, continuous spiral to promote stream 68, flowing in element 62, into a gradual, continuous spiral flow path as it traverses along downstream. The ribbon or spiral-shaped element can have various degrees of curvature along its length. For example, the ribbon can have a first region having a high pitch density adjacent a second region having a low pitch density. The pitch density can be controlled by, for example, varying, i.e. increasing or decreasing, the amount of twist imparted on the ribbon as it is being installed. Thus, in accordance with one or more embodiments of the invention, element 66 can have a constant or variable pitch as installed along the length of element 62.

The spiral-shaped element may comprise a ribbon having an aspect ratio, defined as the width relative to thickness that is greater than about 5 greater than about 10, or even greater than about 20. For example, the spiral-shaped element can have width that is five times its thickness. The particular aspect ratio would vary depending on the mechanical properties necessary during installation and operation of the spiral-shaped element.

FIG. 4 shows a portion of heating element 62 having a spiral-shaped element 66 disposed therein. In the embodiment illustrated in FIG. 4, element 66 spans the entire illustrated length of heating element 62. Element 66 can span the entire length of element 62 or a portion thereof. Moreover, element 66 can comprise a single, unitary structure or a plurality of spiral-shaped elements. And in other embodiments, heating element 62 can comprise a series of disconnected, discrete spiral-shaped elements disposed along at least a portion of the length of heating element 62. As such, heating element 62, for example, can have regions having, disposed therealong, a spiral-shaped element adjacent to regions having free of any spiral-shaped element. As used herein, the term "unitary" refers to a single component rather than an assembly.

In accordance with one or more embodiments of the present invention, heating element 62 comprises a heating tube utilizable in processing mixed-phase material, such as biomaterial or stillage streams. For example, in operation, stillage would be introduced within heating element 62 and heated as the stillage traverses therethrough. As shown in FIG. 4, heating element 62 can comprise spiral-shaped element 66 that can induce stillage stream 68 into a spiral flow path, as indicated by reference 70, to eliminate or at least reduce any boundary layer phenomena near the walls of heating element 62. Consequently, the stillage flowing therethrough would tend to have a homogeneous temperature profile and, significantly, become more homogeneous relative to stillage under similar conditions having laminar flow characteristics. The consequential effect would improve heat transfer rate without an associated increase in effective heat transfer area. Significantly, reduced operating costs can also be realized because of improved heating efficiencies. Reduced operating costs can also be attributed on a system-wide basis. For example, in a grain ethanol processing system, improved heat transfer lends improvements pertinent to drying operations. As heat transfer efficiencies improve, lower heating loads would be realized with consequently lower operating costs. Moreover, improved heat transfer efficiencies would translate to an increase in the effective processing capacity of the drying unit operations and/or reduced environmental emissions. Such improvements can also delay any anticipated capital improvements. For example, in a typical grain ethanol processing facility, stillage concentration to drying unit operations can be increased by about 60% or more, effectively delaying any upgrades until such capacity is exceeded. Reduced overall processing loads typically also reduce operating costs associated with cleaning, maintenance and repair costs.

Flow of the stream within heating element 62 can range from about 2 to about 12 or more feet per second. However, the present invention is not limited to a particular range of stream velocities and would be applicable in operations including laminar and turbulent flow characteristics. It is believed that as the velocity increases, heat transfer increases. However, the increased flow velocity may require increased power loads, typically in the form of increased pump horsepower, especially for highly viscous fluids.

Element 66 can be constructed of any material that is suitable for use in the target environment. Selection of materials of construction would depend on several considerations including, but not limited to service conditions, temperature stability, corrosion stability, cost, corrosion resistance, and ease of installation and replacement. Suitable materials of construction include, for example, carbon steel, stainless steel, and titanium as well as alloys thereof and even thermosetting or thermoplastic polymeric materials such as polypropylene, polyphenylene, polyethylene, polystyrene as well other copolymers or blends thereof. Element 66 may be comprise a material that is chemically inert to the wetting or service stream. In some embodiments, element 66 can comprise the same material of construction as the heating element 62.

Those skilled in the art would readily appreciate and apply the invention described herein to the various unit operations described. Examples of particular equipment, apparatus, and systems constituting the unit operations described are readily available. For example, the design, installation, and/or operation of grinding, centrifugation, distillation, drying, filtration unit operations have been described in, for example, Perry's Chemical Engineer's Handbook, which is incorporated herein by reference in its entirety. Further, those skilled in the art would readily appreciate that the parameters and configurations described herein are exemplary and that actual parameters and configurations will depend upon the specific application for which the system and methods utilizing the spiral-shaped element are used. For example, the spiral-shaped element can have sections of differing pitch, width or both, as well as various combination thereof, along its length. Furthermore, the invention has been described relative to heating a mixed-phase stream; however, the present invention contemplates cooling the mixed-phase stream in a cooling element, i.e. rather than a heating element. The present invention is directed to each feature, system, or method described herein as well as to any combination of two or more such features, systems or methods, so long as they are not mutually inconsistent. For example, a plurality of spiral-shaped elements may be utilized in a heating element or, a spiral-shaped element may span portions of a heating element. Further modifications and equivalents of the invention disclosed herein will occur to persons skilled in the art using no more than routine experimentation and all such modifications and equivalents are believed to be within the spirit and scope of the invention as defined by the following claims.

What is claimed:

1. A system for processing a biomaterial stream comprising a biomaterial source in communication with a heat exchanger including a heater tube wherein the heater tube forms a heating element for heating the biomaterial stream as the biomaterial stream is conveyed through the heater tube; and a spiral-shaped element extending through a substantial portion of the heater tube and configured to cause a substantial portion of the biomaterial stream to move in a generally spiral path through the heater tube, and wherein the heater tube heats the biomaterial stream moving in the spiral path through the heater tube wherein the spiral shaped element is fixed relative to the heater tube.

2. The system as set forth in claim 1, wherein the spiral-shaped element has a width spanning less than about 50% of an inside diameter of the heater tube.

3. The system as set forth in claim 1, wherein the biomaterial source comprises a grain processing facility.

4. The system as set forth in claim 3, wherein the grain processing facility comprises at least one of grain handling, fermentation, distillation and dehydration unit operations.

5. The system of claim 1 wherein the spiral shaped element extends adjacent an interior portion of the heater tube and is configured to leave an unobstructed central opening through the heater tube interiorly of the spiral shaped element.

6. The system of claim 5 wherein the spiral shaped element assumes a generally ribbon configuration throughout a portion of the heater tube.

7. The system of claim 1 including a transfer unit for delivering the biomaterial stream to the heat exchanger.

8. The system of claim 1 wherein the spiral shaped element includes at least two regions with each region having a different pitch density.

9. The system of claim 1 wherein the spiral shaped element includes an aspect ratio of about 5-20.

10. The system of claim 6 wherein the spiral shaped element includes a twist of at least one rotation.

11. The system of claim 1 including a grain steeping unit operation; a grinding unit operation downstream of the grain steeping unit operation; a germ separation unit operation downstream of the grinding unit operation; filtration and washing unit operations receiving material from the germ separation unit operation; and wherein the heat exchanger is operative to receive a heavy steep stream from the grain steeping unit operation.

12. The system of claim 1 including a grain handling unit operation; a grain fermentation unit operation in communication with the grain handling unit operation; a distillation unit operation in communication with the fermentation unit operation; an evaporation unit operation in communication with the distillation unit operation; and a concentrator in communication with the evaporation unit operation, and wherein the concentrator includes the heater tube and spiral shaped element extending through a portion of the heater tube.

13. The system of claim 1 wherein the spiral shaped element winds around an interior wall of the heater tube and is disposed outwardly of a central opening that extends through the heater tube.

14. The system of claim 1 wherein the heat exchanger includes an outer shell that defines a heating medium chamber between the shell and the heater tube; and wherein the heating element is heated by a heating medium in chamber.

15. The system of claim 14 wherein the spiral shaped element winds around an interior wall of the heater tube and is disposed outwardly of a central opening that extends through the heater tube.

* * * * *

UNITED STATES PATENT AND TRADEMARK OFFICE

CERTIFICATE OF CORRECTION

PATENT NO. : 7,572,627 B2
APPLICATION NO. : 10/619280
DATED : August 11, 2009
INVENTOR(S) : Rieke et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1102 days.

Signed and Sealed this

Seventh Day of September, 2010

David J. Kappos

*Director of the United States Patent and Trademark Office*